United States Patent [19]
Aoki et al.

[11] Patent Number: 5,094,817
[45] Date of Patent: Mar. 10, 1992

[54] APPARATUS FOR QUANTITATIVE DETERMINATION OF TRIHALOMETHANES

[75] Inventors: Toyoaki Aoki; Kouji Kawakami, both of Osaka; Yoshiharu Tanaka; Hiroshi Hoshikawa, both of Kanagawa, all of Japan

[73] Assignee: Fuji Electric Co., Ltd., Kanagawa, Japan

[21] Appl. No.: 538,002

[22] Filed: Jun. 14, 1990

Related U.S. Application Data

[62] Division of Ser. No. 303,221, Jan. 30, 1989, Pat. No. 4,960,711.

[30] Foreign Application Priority Data

Jan. 30, 1988 [JP] Japan ................. 63-21061
Jan. 17, 1989 [JP] Japan ................. 1-8302

[51] Int. Cl.$^5$ .............. G01N 21/64; G01N 33/52; G01N 1/18; B01D 63/00
[52] U.S. Cl. .................. 422/68.1; 210/175; 210/321.75; 210/321.8; 422/82.05; 422/82.09; 422/101; 422/256; 436/124; 436/125; 436/126; 436/178
[58] Field of Search .......... 422/68.1, 82.05, 82.08, 422/101, 256; 436/124, 125, 126, 178; 210/640, 641, 500.21, 902, 175, 321.75, 321.8

[56] References Cited

U.S. PATENT DOCUMENTS

| | | | |
|---|---|---|---|
| 4,311,594 | 1/1982 | Perry | 210/640 |
| 4,391,775 | 7/1983 | Huber et al. | 436/126 X |
| 4,666,672 | 5/1987 | Miller et al. | 436/126 X |
| 4,765,963 | 8/1988 | Mukogawa et al. | 422/68.1 |
| 4,929,562 | 5/1990 | Anderson et al. | 422/58 X |

OTHER PUBLICATIONS

Okumura, K. et al., "Fluorimetric Determination of Chloroform in Drinking Water", Analysis, vol. 1, pp. 1498-1502, Dec. 1982.

Primary Examiner—Robert J. Warden
Assistant Examiner—Arlen Soderquist
Attorney, Agent, or Firm—Finnegan, Henderson, Farabow, Garrett and Dunner

[57] ABSTRACT

An apparatus for quantitative determination of trihalomethanes comprises a separation unit containing two channels in contact with each other via a microporous membrane that will not react with trihalomethanes, a reaction unit for heating a carrier solution that has passed through the separation unit, a cooling unit for cooling the carrier solution that has undergone complete reaction; and a detection unit for determining the quantity of a fluorescent substance in the carrier solution. A method for quantitative determination of trihalomethanes comprises flowing a sample solution or a mixture thereof with a reducing agent through one of the two channels in the separation unit, flowing the carrier solution through the other channel, heating the carrier solution that has passed through the separation unit and to which an alkaline nicotinamide or a derivative thereof has been added, cooling the carrier solution, and subjecting the cooled solution to fluorimetry.

5 Claims, 4 Drawing Sheets

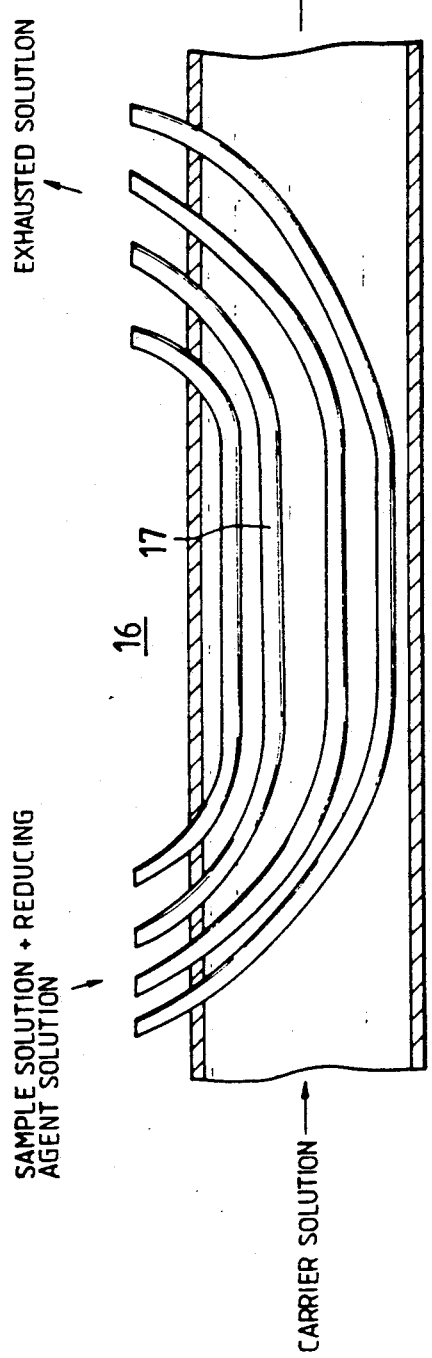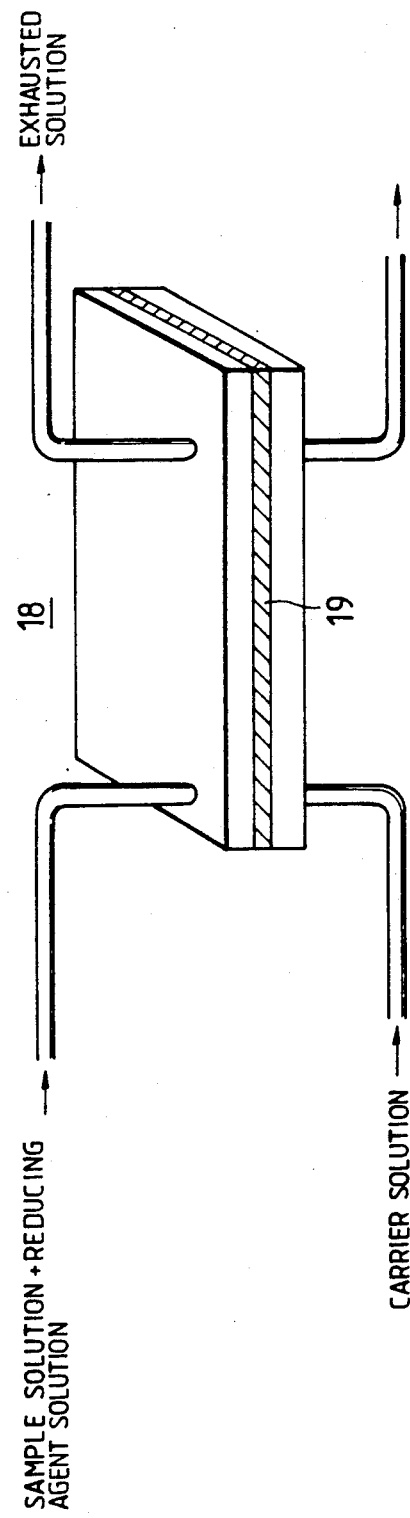

APPARATUS FOR QUANTITATIVE DETERMINATION OF TRIHALOMETHANES

This is a division of application Ser. No. 07/303,221, filed Jan. 30, 1989, now U.S. Pat. No. 4,960,711.

BACKGROUND OF THE INVENTION

The present invention relates to a method and apparatus for quantitative determination of trihalomethanes. More particularly, the present invention relates to a method and apparatus that enables continuous quantitative determination of trihalomethanes without any adverse effects of interfering components.

It has recently been established that trihalomethanes are present in tap water, both in raw and finished states, and this has become a great concern to society because of the potential carcinogenity and mutagenicity of trihalomethanes.

To deal with this problem, the FDA of the United States of America conducted a nationwide survey of total trihalomethane contents in tap water and adopted a regulation requiring that a maximum tolerable level of total trihalomethane contents in tap water should be 100 ppb.

In Japan, too, the Ministry of Public Welfare notified an interim guideline on trihalomethanes in March 1981, which required that the target value of total trihalomethane contents to be controlled should not exceed 100 ppb. Under the circumstances described above, there has been a growing need for the correct measurement of trihalomethanes.

Trihalomethanes can be measured by gas chromatography and the following three methods have been adopted to date: (1) purge-trap; (2) solvent extraction; and (3) headspace.

However, these conventional methods have various problems, such as the need to perform preliminary treatments that are complicated and time-consuming, and inability to conduct continuous measurements.

A technique has recently been proposed that fluorimetric determination of chloroform in water be conducted by utilizing the Fujiwara reaction which involves reaction between alkaline nicotinamide and chloroform to produce a fluorescent condensation compound (Okumura K. et al., Analyst, 107, pp. 1498-1502, 1982). However, this method is not suitable for practical applications since if it is directly applied to tap water in either the raw or finished state, many problems will occur, such as (1) inability to provide correct results on account of the presence of interfering substances and (2) inability to conduct continuous measurements.

SUMMARY OF THE INVENTION

The present invention has been accomplished under these circumstances and the principal object thereof is to provide a method and apparatus which enable trihalomethanes in water to be continuously assayed without adverse affects of interfering substances.

A method for quantitative determination of trihalomethanes in accordance with the present invention, comprises: allowing a sample solution or a mixture thereof with a reducing agent to flow through one of the two channels in a membrane separator, that are in contact with each other via a microporous membrane that will not react with trihalomethanes; allowing a carrier solution to flow through the other channel, the carrier solution being such that an alkaline nicotinamide or a derivative thereof that will react with trihalomethanes is to be added; heating the carrier solution that has passed through the membrane separator and to which an alkaline nicotinamide or a derivative thereof has been added; cooling said carrier solution; and subjecting the cooled solution to fluorimetry.

An apparatus for quantitative determination of trihalomethanes in accordance with the present invention, comprises: a separation unit containing two channels in contact with each other via a microporous membrane that will not react with trihalomethanes, a sample solution or a mixture thereof with a reducing agent being allowed to flow through one of the channels while a carrier solution, to which a substance that reacts with trihalomethanes is to be added, being allowed to flow through the other channel; a reaction unit for heating the carrier solution that has passed through the separation unit and to which the substance that reacts with trihalomethanes has been added; a cooling unit for cooling the carrier solution that has undergone complete reaction; and a detection unit for determining the quantity of a fluorescent substance in the carrier solution. The microporous membrane in the separation unit may be composed of a plurality of hollow fibers or a polymeric membrane held in tabular form.

A sample solution containing trihalomethanes or a mixture of such a sample solution with a reducing agent is allowed to flow through one of the two channels in the membrane separator. A reducing agent is added in order to decompose any oxidizers (e.g. chlorine and chloramine) that may be present in the sample solution. An alkaline nicotinamide or a derivative thereof will react with trihalomethanes to form a fluorescent condensation product. The fluorescent condensate is generated under an alkaline condition, so that trihalomethanes are reacted with nicotinamide under alkaline conditions.

Trihalomethanes in water are volatile and are capable of permeating in gaseous form through a microporous membrane. The permeating trihalomethanes dissolve in the carrier solution to be separated from suspended solids, ions and various other substances in water that will interfere with the intended analysis. Operations with the membrane separator can be performed continuously. The fluorescent condensate obtained by reaction between trihalomethanes and nicotinamide or a derivative thereof can be determined continuously by fluorimetry.

BRIEF DESCRIPTION OF THE DRAWINGS

FIG. 3 is a schematic cross section showing a permeation unit used in another embodiment of the present invention;

FIG. 4 is a schematic perspective view showing a permeation unit used in still another embodiment of the present invention;

DETAILED DESCRIPTION OF THE PREFERRED EMBODIMENTS

Embodiments of the present invention will be described below with reference to the accompanying drawings.

Figure 1:
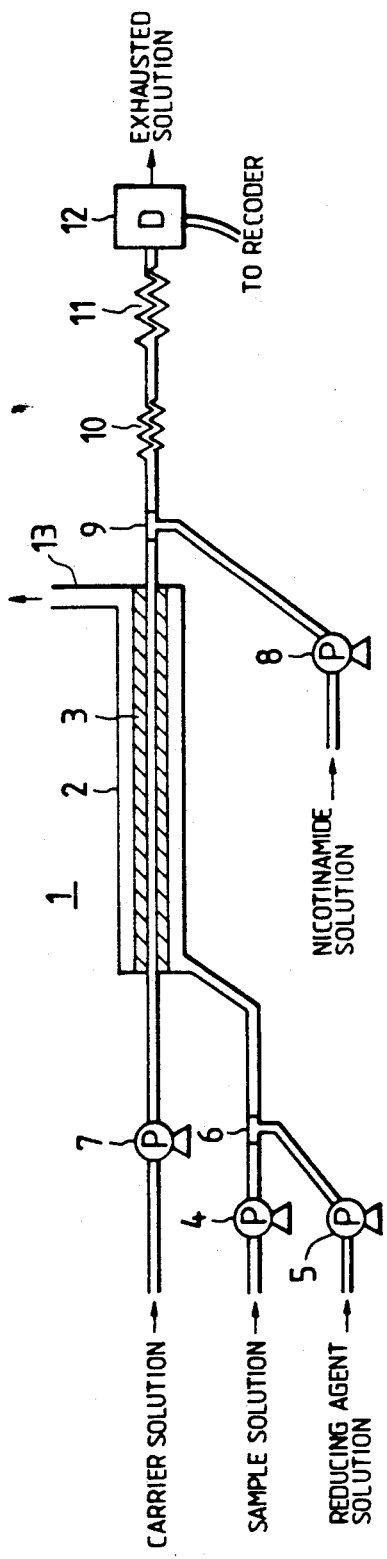
FIG. 1 is a schematic cross section for explaining a method for quantitative determination of trihalomethanes in water according to one embodiment of the present invention.

FIG. 1 is a schematic view for explaining a method of assaying trihalomethanes in accordance with one embodiment of the present invention. Shown by 1 is a permeation unit as a double-walled structure consisting of an outer Teflon tube 2 (Teflon is the trade name of Du Pont for polytetrafluoroethylene) and an inner microporous Teflon tube 3. The inner microporous Teflon tube 3 may be formed of TB Series (porosity, 70%; maximum pore size, 3.5 $\mu$m) made by Japan Gore-Tex Co., Ltd. To take TB001 as an example, it has an inside diameter of 1 mm and an outside diameter of 1.8 mm. The length of the microporous Teflon tube 3 influences the sensitivity of analysis, so it should be used in an appropriate length, say, 40 cm.

The sample solution sent by a pump 4 and is mixed at a three-way joint 6 with a solution of a reducing agent such as sulfurous acid or thiosulfuric acid that is being sent by a pump 5. The reducing agent decomposes chlorine, chloramine or other oxidizers in the sample solution and the mixture is sent to the outer Teflon tube 2 in the permeation unit 1. A carrier solution is injected into the microporous Teflon tube 3 by a pump 7. The carrier solution is rendered alkaline by addition of sodium hydroxide. The carrier solution incorporates the permeating trihalomethanes and is mixed at a three-way joint 9 with a nicotinamide solution being sent by a pump 8. The mixture is heated with a reaction coil 10 submerged in boiling water, then cooled with a reaction coil 11 submerged in ice water. The cooled mixture is sent to a fluorescence detector 12 which produces an output signal on a recorder.

Alternatively, a nicotinamide solution may be used as a carrier solution which is mixed with a sodium hydroxide solution being sent by the pump 8.

If desired, a mixed solution of sodium hydroxide and nicotinamide may be sent as a carrier solution by the pump 7. In this case, the exit end of the microporous Teflon tube 3 is directly connected to the reaction coil 10.

In still another embodiment, the carrier solution may be allowed to flow outside the microporous Teflon tube 3 whereas the mixture of the sample solution and the solution of reducing agent is allowed to flow within the tube. In this case, the pump 8 for supplying the nicotinamide solution and the reaction coil 10 must be connected to the effluent side 13.

Figure 2:
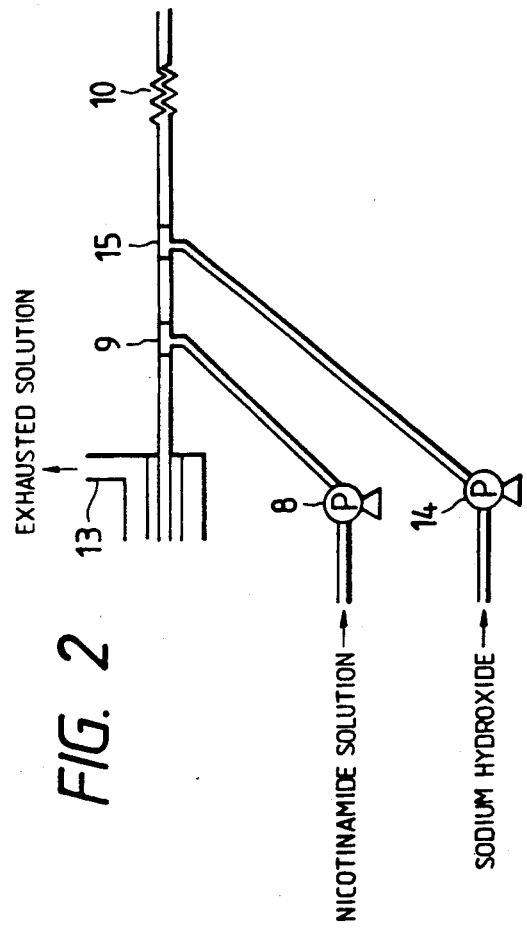
FIG. 2 is a schematic cross section for explaining a method according to a modification of the embodiment shown in FIG. 1.

Distilled water or ion-exchanged water which is capable of dissolving trihalomethanes may be used as a carrier solution. In this case, the carrier solution emerging from the microporous Teflon tube 3 may be mixed with a nicotinamide solution and a sodium hydroxide solution at three-way joints 9 and 15, respectively, as shown in FIG. 2, and then the mixture is sent to the reaction coil 10. In this case, too, the order of adding the nicotinamide and sodium hydroxide solutions to the carrier solution may be reversed. If desired, a mixture of the two solutions may be added to the carrier solution.

FIG. 3 shows a permeation unit 16 for use in still another embodiment of the present invention. A bundle of hollow fibers 17 are used in such a way that a mixture of the sample solution and a solution of reducing agent is allowed to flow through the hollow fibers 17 whereas the carrier solution flows outside the fibers. Alternatively, the carrier solution may be allowed to flow through the hollow fibers 17 whereas the mixed solution flows outside the fibers. The microporous hollow fibers 17 are preferably made of Teflon or acetyl cellulose in tubular form having an outside diameter of 1 mm and a pore size of 1-3 $\mu$m. The use of hollow fibers offers the advantage of increasing the sensitivity of trihalomethane detection.

FIG. 4 shows a permeation unit 18 in a further embodiment of the present invention wherein a microporous polymeric membrane 19 is held in tabular form between an upper and a lower compartment. A mixture of the sample solution and a solution of reducing agent is guided into the upper compartment whereas the carrier solution is guided into the lower compartment. Alternatively, the mixed solution may be directed into the lower compartment and the carrier solution into the upper compartment.

Figure 5:
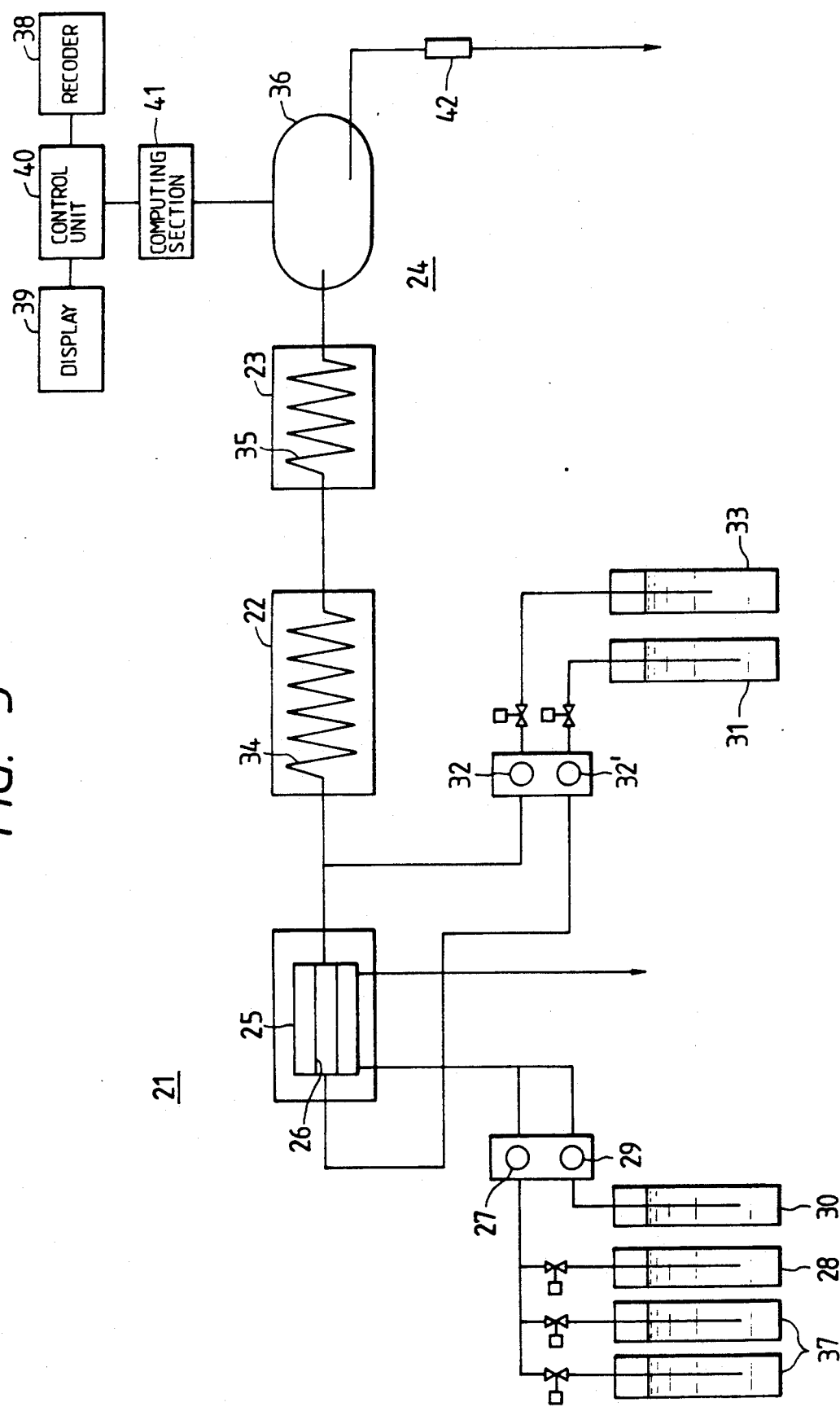
FIG. 5 is a schematic view showing an analytical apparatus for determining the quantity of trihalomethanes in water in accordance with one embodiment of the present invention.

FIG. 5 is a schematic view of an analytical apparatus according to one embodiment of the present invention. The apparatus comprises a separation unit 21, a reaction unit 22, a cooling unit 23, and a detection unit 24 including a fluorescence detector 36 and a computing section 41.

The separation unit 21 is formed as a double-walled structure, as in FIG. 1, consisting of an outer Teflon tube 25 and an inner microporous Teflon tube 26. The inner microporous Teflon tube 26 may be formed of the TB Series (porosity, 70%; maximum pore size, 3.5 $\mu$m) made by Japan Gore-Tex Co., Ltd. The entire part of the separation unit is held at a constant temperature of 50° C., at which the permeation of trihalomethanes in the sample into the carrier solution attains a maximum.

The sample solution 28 as being sent by a pump 27 is mixed with a solution 30 of a reducing agent such as sulfurous acid or thiosulfuric acid that is being sent by a pump 29. The reducing agent decomposes chlorine, chloramine or other oxidizers in the sample solution and the mixture is sent to the outer Teflon tube 25 in the separation unit 21. A carrier solution 31 is injected into the microporous Teflon tube 26 by a pump 32'. The carrier solution is rendered alkaline by addition of sodium hydroxide at a concentration of 0.2–0.4 M. The carrier solution incorporates the permeating trihalomethanes and is mixed with a nicotinamide solution 33 being sent by a pump 32. The mixture is heated with a reaction coil 34 submerged in boiling water, and subsequently cooled with a reaction coil 35 submerged in ice water. The cooled mixture is sent to a fluorescence detector 36, whose output is compared with stored calibration lines that have been constructed for standard trihalomethane solution 37 by similar procedures. As a result of this comparison, the concentrations of trihalomethanes in the sample are calculated in the computing section 41, recorded in a recorder 38 and displayed on a display 39. All the operations described above are controlled by a control unit 40. The carrier solution is discharged from the fluorescence detector 36, and a back pressure coil 42 is provided to prevent the carrier solution from pulsating.

The concentration of the nicotinamide solution which is to be reacted with trihalomethanes, influences the intensity of fluorescence, or the amount of fluorescent condensate which is produced as a result of reaction between trihalomethanes and nicotinamide, and the higher the concentration of the nicotinamide solution, the higher the intensity of fluorescence that is attained. Therefore, the nicotinamide solution used is desirably an almost saturated aqueous solution having a concentration of 40%.

Figure 6:
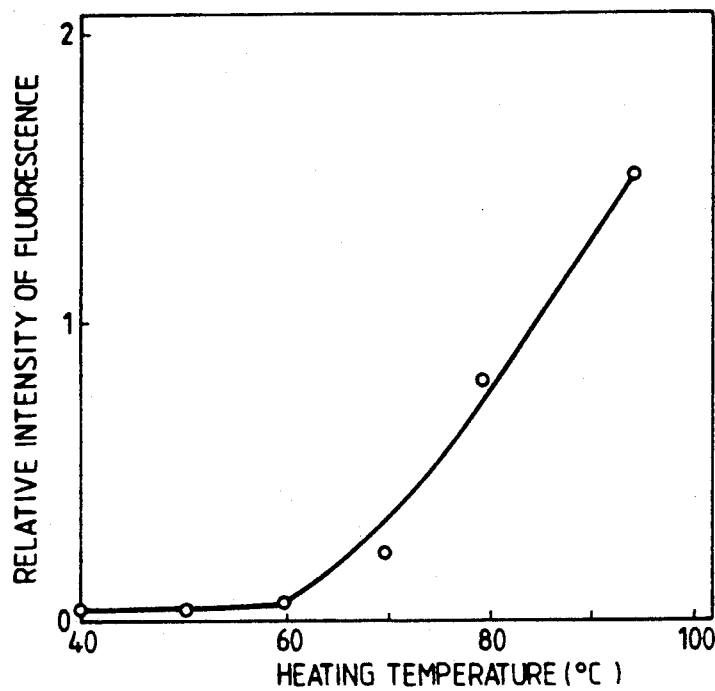
FIG. 6 is a graph showing the relationship between the relative intensity of fluorescence and the heating temperature used in the reaction between nicotinamide and trihalomethanes.

As shown in FIG. 6, the intensity of fluorescence increased as the reaction coil was heated to a temperature higher than 60° C. However, above 95° C., dissolved oxygen in the reaction solution evaporated and the resulting air bubbles caused background noise to increase. Therefore, the temperature at which the reaction coil is heated is desirably between 95° and 98° C.

The cooling unit is provided so that the sensitivity of analysis will not be lowered on account of thermal extinction of the fluorescence emitted from the fluorescent condensation product formed of trihalomethanes and nicotinamide which is formed in the reaction unit. This cooling unit is desirably held at a temperature in the range of 0°-20° C.

The intensity of fluorescence from the reaction product is desirably measured at 450-470 nm with excitation at 360-380 nm.

Figure 7:
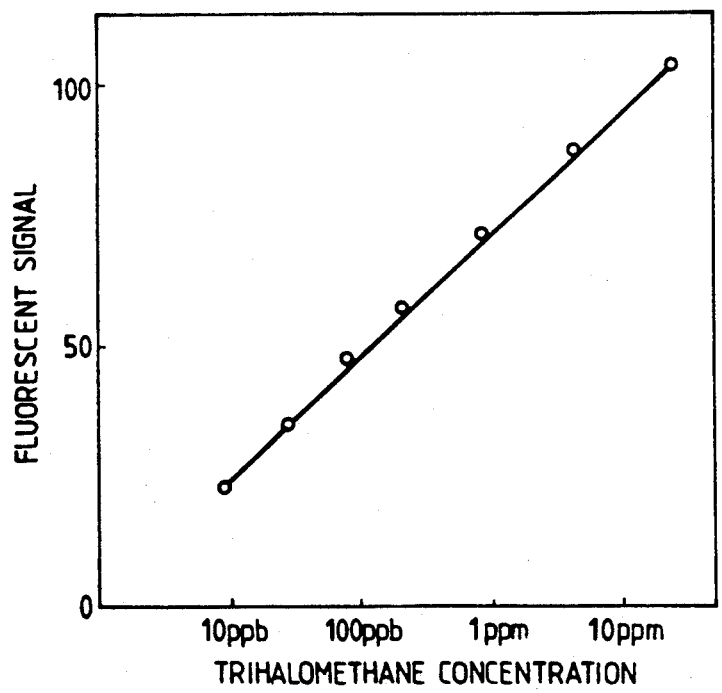
FIG. 7 is a graph showing the correlation between trihalomethane concentration and fluorescence intensity in accordance with one embodiment of the present invention.

FIG. 7 shows a calibration line plotting the correlation between trihalomethane concentration and the intensity of fluorescent signal from the fluorescence detector. Good linearity was established in the trihalomethane concentration range of 10 ppb-20 ppm.

The effects of potential interfering substances in tap water are summarized in Table 1 below, from which one can see that the interferences of most of the substances present in tap water were substantially eliminated by the combined effects of the separation unit 21 and the addition of a reducing agent, thereby enabling precise determination of the concentrations of trihalomethanes (THMs) in tap water.

TABLE 1

| Contaminant | Reducing agent not added but separation unit employed (THM concentration, ppb) | Reducing agent added but separation unit not employed (THM concentration, ppb) | Reducing agent used and separation unit employed (THM concentration, ppb) |
| --- | --- | --- | --- |
| Cholorine (7 mg/l) | 0.5 | N.D | N.D |
| Monochloramine (7 mg/l) | 88.3 | N.D | N.D |
| Dichloramine (7 mg/l) | 11.8 | N.D | N.D |
| Calcium ion (50 mg/l) | N.D. | N.D | N.D |
| Chloride ion (50 mg/l) | N.D. | N.D | N.D |
| Humic acid (2 mg/l) | N.D. | 37 | N.D |
| Humic acid (10 mg/l) | N.D. | 138 | N.D |

N.D: not detected

As described above, according to the present invention, trihalomethanes in a sample solution can be determined continuously to very low levels without being interfered by other substances.

When tap water is used as a sample solution, monochloramine and dichloramine in it will permeate through the microporous membrane to interfere with the intended analysis. However, this problem can be solved by decomposing the chloramines with an added reducing agent in solution.

When a mixed solution of alkaline nicotinamide with trihalomethanes which permeate through the microporous membrane, is heated and cooled and if the resulting solution is subjected to fluorimetry, trihalomethanes present in quantities of no less than 0.8 ppb in the solution can be selectively assayed by the method of the present invention, with a signal-to-noise ratio of 3 being assumed as the lower limit of assaying. The method and apparatus of the present invention also enables the intended assay of trihalomethanes in water to be completed rapidly within about 8 minutes.

What is claimed is:

1. An apparatus for quantitative determination of trihalomethanes, comprising:
   a first tube portion for flowing a carrier fluid;
   a second tube portion for flowing a sample solution;
   a separation unit including a first channel for the carrier fluid from the first tube portion and a second channel for the sample solution from the second tube portion;
   a microporous membrane provided between and connecting the first channel with the second channel;
   a third tube portion, in fluid communication with the second channel, for flowing sample solution away from the separation unit;
   a fourth tube portion, in fluid communication with said first channel, for flowing said carrier fluid from said separation unit;
   a fifth tube portion, in fluid communication with said fourth tube portion, for introducing a substance which reacts with trihalomethanes to the carrier fluid;
   a reaction unit for receiving the carrier fluid from the fifth tube portion and for heating the carrier fluid to which the substance that reacts with trihalomethanes has been introduced;
   a cooling unit for receiving the heated carrier fluid and for cooling the carrier solution; and
   a fluorescence detection unit, receiving the cooled carrier fluid, for determining a quantity of fluorescent substance in the carrier fluid.

2. The apparatus of claim 1, further comprising a sixth tube portion in fluid communication with the second tube portion for introducing a reducing agent into the sample solution.

3. The apparatus of claim 2, further comprising a seventh tube portion in fluid communication with the fifth tube portion for flowing sodium hydroxide into the carrier fluid mixed with the substance that reacts with trihalomethanes.

4. An apparatus according to claim 1, wherein the microporous membrane comprises a plurality of hollow fibers.

5. An apparatus according to claim 1, wherein the microporous membrane comprises a polymeric membrane held in tabular form.

* * * * *